(12) United States Patent
Anton et al.

(10) Patent No.: US 9,532,760 B2
(45) Date of Patent: Jan. 3, 2017

(54) X-RAY DEVICE

(71) Applicant: Siemens Aktiengesellschaft, Munich (DE)

(72) Inventors: Gisela Anton, Erlangen (DE); Oliver Preusche, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 220 days.

(21) Appl. No.: 14/387,254

(22) PCT Filed: Apr. 16, 2013

(86) PCT No.: PCT/EP2013/057912
§ 371 (c)(1),
(2) Date: Sep. 23, 2014

(87) PCT Pub. No.: WO2013/160153
PCT Pub. Date: Oct. 31, 2013

(65) Prior Publication Data
US 2015/0055744 A1  Feb. 26, 2015

(30) Foreign Application Priority Data

Apr. 24, 2012 (DE) ........................ 10 2012 008 204

(51) Int. Cl.
*A61B 6/00* (2006.01)
*G21K 1/06* (2006.01)

(52) U.S. Cl.
CPC ............. *A61B 6/484* (2013.01); *A61B 6/4291* (2013.01); *G21K 1/065* (2013.01); *A61B 6/4233* (2013.01);

(Continued)

(58) Field of Classification Search
CPC .... A61B 6/484; G21K 1/065; G21K 2207/005
See application file for complete search history.

(56) References Cited

U.S. PATENT DOCUMENTS 8,214,158 B2 *   7/2012   Mukaide ................ A61B 6/484
                                                              702/172
8,588,366 B2 * 11/2013   Mukaide ................ A61B 6/484
                                                              378/154

(Continued)

FOREIGN PATENT DOCUMENTS

CN         1527048 A         9/2004
DE   10 2006 015 355 A1      8/2007

(Continued)

OTHER PUBLICATIONS

Weitkamp, Timm et al.; "X-ray phase imaging with a grating interferometer"; Optics Express, vol. 13, No. 16, published Aug. 8, 2005, pp. 6296-6304; Optical Society of America; 2005: Aug. 8, 2005.

(Continued)

*Primary Examiner* — Thomas R Artman
(74) *Attorney, Agent, or Firm* — Harness, Dickey & Pierce, P.L.C.

(57) ABSTRACT

An embodiment of the invention relates to an X-ray device, more particularly for phase-contrast imaging in the medical sector. In at least one embodiment, the X-ray device includes an X-ray radiation source, a coherence grid, a phase grid and an X-ray detector from a number of pixels arranged in a matrix, the pixels including a lens grid.

16 Claims, 10 Drawing Sheets

(52) U.S. Cl.
CPC ......... *A61B 6/502* (2013.01); *G21K 2207/005* (2013.01)

(56) References Cited

U.S. PATENT DOCUMENTS

| | | | | |
|---|---|---|---|---|
| 8,638,903 | B2* | 1/2014 | Mukaide | G21K 1/06 378/159 |
| 8,644,449 | B2* | 2/2014 | Mukaide | G21K 1/06 378/159 |
| 9,234,856 | B2* | 1/2016 | Mukaide | G01N 23/04 |
| 9,329,141 | B2* | 5/2016 | Stutman | G01N 23/046 |
| 2011/0064196 | A1* | 3/2011 | Mukaide | G21K 1/06 378/62 |
| 2011/0103549 | A1* | 5/2011 | Mukaide | G21K 1/06 378/62 |
| 2011/0158389 | A1* | 6/2011 | Mukaide | A61B 6/484 378/62 |
| 2011/0194674 | A1* | 8/2011 | Mukaide | G01N 23/046 378/62 |
| 2013/0108020 | A1* | 5/2013 | Mukaide | G01N 23/04 378/62 |
| 2013/0315373 | A1* | 11/2013 | Rossl | G21K 1/06 378/62 |
| 2015/0055744 | A1* | 2/2015 | Anton | G21K 1/065 378/36 |
| 2016/0066873 | A1* | 3/2016 | Preusche | A61B 6/4035 378/36 |

FOREIGN PATENT DOCUMENTS

| | | |
|---|---|---|
| DE | 10 2006 015 356 A1 | 8/2007 |
| DE | 10 2006 015 358 A1 | 8/2007 |
| DE | 10 2006 017 290 A1 | 8/2007 |
| DE | 10 2006 017 291 A1 | 8/2007 |
| DE | 10 2006 037 281 A1 | 8/2007 |
| EP | 1 447 046 A1 | 8/2004 |
| WO | WO 2008102632 A1 | 8/2008 |

OTHER PUBLICATIONS

Pfeiffer, Weitkamp et al.,Phase retrieval and differential phase-contrast imaging with low-brilliance X-ray sources Nature Physics, vol. 2, pp. 258-261; 2006.

X-ray phase contrast imaging using a grating nterferometer, F. Pfeifer et al.; F. Pfeifer et al., "X-ray phase contrast imaging using a grating nterferometer", Europhysics News, No. 5, vol. 37, pp. 13-15.

Simon Markus; "Röngenlinsen mit großer Apertur"; KIT Scientific Publishing; Schriften des Institus für Mikrostrukturtechnik am Karlsruher Institut für Technologie; vol. 4; pp. 21-93; ISBN: 978-3-86644-530-7; DOI: 10.5445/KSP/1000018510, XP002707766; 2010; DE.

Björn Cederström, "A Multi-Prism Lens for Hard X-Rays", Dissertation, KTH Stockholm, pp. 1-135; 2002; SE.

Boris Benner, "Imaging with Parabolic Refractive X-Ray Lenses", Dissertation, RWTH Aachen, urn:nbn:de:hbz:82-opus-11521, pp. 1-140, 2005; DE.

P. Bartl et al.: Grating-based high energy X-ray interferometry with the Medipix-detector in simulation and measurement, Journal of Instrumentation (JINST) 5, 10008, pp. 17; 2010.

Klaus J. Engel et al.: Contrast-to-noise in X-ray differential phase contrast imaging, Nuclear Instruments and Methods in Physics Research A 648, pp. 202-207; 2011.

Tilman Donath et al.: Phase-contrast imaging and tomography at 60 keV using a conventional x-ray tube source, Review of Scientific Instruments 80, 053701, pp. 7; 2009.

Atsushi Momose: Recent Advances in X-ray Phase Imaging, Japanese Journal of Applied Physics, vol. 44. No. 9A, pp. 6355-6367; 2005; JP.

Thomas Weber et al.: Noise in x-ray grating-based phase-contrast imaging, Med. Phys. 38 (7), Am. Assoc. Phys. Med., pp. 4133-4140; 2011; US; Jul. 1, 2011.

International Search Report and Written Opinion dated Aug. 22, 2013.

Chinese Office Action mailed Mar. 11, 2016.

* cited by examiner

X-RAY DEVICE

PRIORITY STATEMENT

This application is the national phase under 35 U.S.C. §371 of PCT International Application No. PCT/EP2013/057912 which has an International filing date of Apr. 16, 2013, which designated the United States of America, and which claims priority to German patent application number DE 10 2012 008 204.5 filed Apr. 24, 2012, the entire contents of each of which are hereby incorporated herein by reference.

FIELD

At least one embodiment of the invention generally relates to an x-ray device, in particular for phase-contrast imaging in the medical sector, comprising an x-ray radiation source, a coherence grating, a phase grating and an x-ray detector made of a number of pixels disposed in a matrix-like manner.

BACKGROUND

The interaction between electromagnetic radiation, i.e. x-ray radiation as well, and a medium is described, inter alia, with the aid of the complex refractive index. Here, the real part and imaginary part of the refractive index in each case depend on the material composition of the medium to which the complex refractive index is assigned. While the imaginary part reproduces the phenomenon of absorption of electromagnetic radiation in a medium, the real part describes the phenomenon of refraction, which is mainly known from the field of geometric optics.

In principle, both interaction phenomena can be used for an imaging method, for example for medical diagnostics. However, devices for metrological acquisition of the material-dependent absorption are predominantly used at this moment in time, wherein, in so-called x-ray radiography, an object to be examined is irradiated by x-ray radiation and the transmitted intensity downstream of the object to be examined is recorded. On the basis of this measurement, it is possible to make a projection image which reproduces a two-dimensional distribution of the absorption properties of the object. Finally, in x-ray tomography, a multiplicity of projection images are recorded, on the basis of which a three-dimensional data record is then calculated, said three-dimensional data record reflecting the spatial distribution of the absorption coefficients. From this, it is then possible to deduce the spatial distribution of the material composition of the object.

These days, devices for acquiring the phase shift, i.e. the refraction of x-ray radiation, caused by an object to be examined in order to establish the material composition of objects are still less widespread. The corresponding methods, these being referred to as phase contrast radiography and phase contrast tomography, however, are currently subject to intensive research and appropriate devices are increasingly being developed.

Here, the metrological acquisition of the phase shift is generally brought about indirectly by measuring an intensity and an interference condition, wherein the metrological design employed for this is typically based on a Talbot-Lau interferometer. Accordingly, it comprises a number of optical and, in particular, x-ray optical gratings disposed between an x-ray radiation source and an x-ray detector. Such a design enables the implementation of an interferometric measurement method, as emerges from e.g. "X-ray phase imaging with a grating interferometer", T. Weitkamp et al., Optics Express, volume 13, number 16, Aug. 8, 2005.

Further machines for phase-contrast imaging are known, inter alia, from the European patent application EP 1 447 046 A1 and the German patent applications 10 2006 017 290.6, 10 2006 015 358.8, 10 2006 017 291.4, 10 2006 015 356.1 and 10 2006 015 355.3, and various embodiments of x-ray optical gratings are described in e.g. DE 10 2006 037 281 A1.

As mentioned above, the starting point of all known measurement devices is formed by the Talbot-Lau interferometer, in which an x-ray radiation source, a coherence grating $G_0$, a phase grating $G_1$, an analysis grating $G_2$ and an x-ray detector made up of a plurality of pixels are arranged along an optical axis. Here, the coherence grating $G_0$ serves to ensure a sufficient spatial coherence of the x-ray radiation source.

Accordingly, it is possible to dispense with the coherence grating $G_0$ in the case of an x-ray radiation source which, to a good approximation, can be considered to be a point source. An interference pattern is generated with the aid of the phase grating or else a diffraction grating $G_1$, which typically has a uniformly striped structure, wherein the period of this interference pattern is typically significantly smaller than the size of the pixels of the x-ray detector, and therefore direct acquisition of the interference pattern with the x-ray detector is not possible.

Rather, the analysis grating or the absorption grating $G_2$, with the aid of which the interference pattern can, as it were, be sampled by a spatial-periodic masking of x-ray radiation, is arranged upstream of the x-ray detector, and so said interference pattern can be displayed with the aid of the pixels of the x-ray detector. To this end, the analysis grating $G_2$ is displaced in a plane perpendicular to the optical axis and also perpendicular to the stripes of the structure in the case of a uniformly striped structure of the phase grating $G_1$ and intensity measurements are undertaken with the aid of the x-ray detector for different displacement positions.

Alternatively, a stationary arrangement is provided for the analysis grating $G_2$ and the interference pattern is sampled by displacing the coherence grating $G_0$ or the diffraction grating $G_1$.

This basic design can be used for an imaging method, i.e. for phase-contrast imaging, wherein an object to be examined or a patient is positioned e.g. between the coherence grating G0 and/or the x-ray radiation source and the phase grating G1, or between the phase grating G1 and the analysis grating G2 in the vicinity of the phase grating G1. The object to be examined then causes a spatially dependent phase shift of the x-ray radiation passing through the object to be examined, as a result of which changes are generated in the interference pattern which are acquired metrologically by way of the x-ray detector.

In order to establish the phase shift caused by the object to be examined, there a displacement of, for example, the phase grating G1 across the optical axis in discrete steps, wherein the intensity at the x-ray detector is measured in each case. The measurement values acquired thus are then for example compared to sinusoidal curves associated with different phase shifts. In this manner it is then possible to deduce the phase shift caused by the object to be examined.

SUMMARY

At least one embodiment of the invention is directed to an advantageous x-ray device, in particular for phase-contrast imaging.

According to at least one embodiment of the invention, an x-ray device is disclosed. The dependent claims in part contain advantageous developments of at least one embodiment of the invention and in part contain inherently inventive developments of the invention.

In at least one embodiment, the design of the x-ray device is based on the discovery that the phase is quite flat at positions with high intensity, i.e. it only has a small spatially dependent variation in regions with high intensity. By contrast, spatially dependent phase shifts are quite clearly visible in regions in which the intensity is low. The basic concept of integrating a light-refractive lens system into the design is based on this discovery.

The x-ray device is embodied, in at least one embodiment, for the implementation of a phase-contrast imaging method and preferably provided for use in the medical sector. It comprises an x-ray radiation source, a coherence grating, a phase grating and an x-ray detector made of a number of pixels disposed in a matrix-like manner and, moreover, the design of the x-ray device comprises a lens grating.

BRIEF DESCRIPTION OF THE DRAWINGS

Example embodiments of the invention will be explained in more detail below on the basis of a schematic drawing. In detail.

Parts corresponding to one another have in each case been provided with the same reference signs in all figures.

DETAILED DESCRIPTION OF EXAMPLE EMBODIMENTS

The x-ray device is embodied, in at least one embodiment, for the implementation of a phase-contrast imaging method and preferably provided for use in the medical sector. It comprises an x-ray radiation source, a coherence grating, a phase grating and an x-ray detector made of a number of pixels disposed in a matrix-like manner and, moreover, the design of the x-ray device comprises a lens grating.

Here, to a first approximation, the design corresponds to the design of a Talbot-Lau interferometer as set forth at the outset, wherein the analysis grating $G_2$ was replaced by the lens grating. Here, the lens grating acts like a regular arrangement of positive lenses, wherein each one of the positive lenses preferably focuses the x-ray radiation in the scope thereof to precisely 1 pixel of the x-ray detector. Under the assumption of, firstly, line-by-line and, secondly, column-by-column numbering of the pixels of the x-ray detector, each pixel further preferably has its own positive lens which is assigned to the respective pixel, wherein the positive lenses alternately focus on even pixels and odd pixels in, firstly, a line-by-line manner and, secondly, a column-by-column manner. By way of example, this can be realized by placing two gratings rotated by 90° on top of one another.

Alternatively, the lens grating comprises a regular arrangement of columns of positive lenses focusing in one dimension, wherein each one of the columns of positive lenses preferably focuses the x-ray radiation in the scope thereof onto precisely one column of pixels of the x-ray detector. Accordingly, each column of pixels of the matrix-like x-ray detector preferably has its own, assigned positive lens column.

This column-shaped or strip-shaped design of the lens grating is preferably used in combination with a phase grating $G_1$ which is assembled in a strip-shaped manner, wherein the strips of the strip-shaped structure of the phase grating $G_1$ are disposed parallel to the positive lens columns of the lens grating.

In an advantageous development, adjacent positive lens columns respectively mesh such that the edges of the positive lenses of the two adjacent positive lens columns are situated near the center of a positive lens.

Here, the design is preferably configured for obtaining medical differential phase-contrast images by way of x-ray radiation with a photon energy in the range from 10 keV to 100 keV. Here, the usable work range of the spectrum is preferably selected in such a way that the upper limit is spaced from the lower limit by at most a factor of $\sqrt{3}$. Thus, for example, a configuration is envisaged for the 50 keV to 86 keV range or else, e.g. for mammography, for a range of 15 keV to 25 keV. This restriction helps in reducing a negative influence from chromatic aberration to an acceptable amount. The x-ray device preferably serves, in particular, for examining soft tissue and therefore for examining matter which substantially contains atoms with a small atomic number.

Moreover, it has been established that each device that is able to measure phase-contrast images is also able to generate so-called dark-field images from the same raw data, i.e. from the same measurement data. To this end, the raw data are prepared differently, wherein, for example, the measured deviations of the interference pattern positions along the displacement axis are integrated for the phase-contrast image while the local contrast in the interference pattern is visualized directly for the dark image. These two visualization options are both compatible with the structure proposed here and both unchangingly remain possible. Accordingly, an x-ray device presented here is preferably configured in such a way that it can generate both dark-field images and phase-contrast images, wherein both are obtained from the same raw data.

The lens grating is expediently disposed between the phase grating and the x-ray detector and preferably has an extent across the optical axis of the design approximately corresponding to the extent of the phase grating $G_1$. Hence the lens grating modifies the radiation field emanating from the phase grating $G_1$ before said radiation field reaches the x-ray detector.

Furthermore, a focus plane can be associated with the lens grating and the x-ray detector is preferably positioned in this focus plane or offset with a small distance in the direction of the phase grating $G_1$ from the focus plane. Thus, if the lens grating is assembled from a regular arrangement of positive lenses, a focus point, more precisely a wavelength-dependent focus point, can be assigned to each positive lens and the focus points of all positive lenses lie, to a good approximation, in a plane which is then considered to be a focus plane. This focus plane is aligned perpendicular to the optical axis and accordingly aligned parallel to the pixels of the x-ray detector, to the coherence grating and to the phase grating. Moreover, the design is preferably configured in such a way that the pixel centers of the x-ray detector coincide with the focus points such that it is then possible to dispense with an analysis grating $G_2$. By way of example, this can almost halve the x-ray dose to which a patient is exposed during an examination.

In accordance with an embodiment variant of the x-ray device, the latter additionally comprises an analysis grating or absorption grating $G_2$ which is positioned between the lens grating and the x-ray detector. This analysis grating is preferably positioned in the focus plane of the lens grating or offset from the focus plane by a small distance in the direction of the phase grating $G_1$, and moreover aligned parallel to the lens grating. This design follows the Talbot-Lau interferometer described at the outset, but the additional use of the lens grating allows for coarsening, i.e. a coarser embodiment, of the structure of the analysis grating $G_2$ and, correspondingly, a longer grating period $p_2$. As a result of the longer grating period $p_2$, the height $h_2$ of the analysis grating $G_2$, i.e. the extent in the direction of the optical axis, which can be achieved by manufacturing is also higher since it is predominantly restricted by the aspect ratio $r=h/(p/2)$ achievable during production. In this context, the aspect ratio r is currently restricted to approximately 50 in the case of production by way of reactive ion etching and approximately 100 when using a LIGA method. The height h in turn has an effect on the absorption capability of the analysis grating $G_2$ and therefore has an effect on how well the spatial/periodic masking of the x-ray radiation field by the analysis grating $G_2$ works. This has a direct effect on the so-called visibility and hence also on the achievable image quality during phase-contrast imaging. By coarsening the structure of the analysis grating $G_2$, a sufficient height h can be realized in a much simpler manner and it is therefore possible to achieve improved visibility. This is advantageous because, in particular, the required x-ray dose for a given image quality is inversely proportional to the square of the visibility. Accordingly, the visibility is more important to the required x-ray dose than the absorption by the grating assemblies.

If use is made of both an analysis grating comprising a strip-shaped structure made of grating webs and slits, and also the lens grating comprising positive-lens columns, the positive-lens columns preferably focus alternately onto the grating webs and the slits. In the case of simple continuous numbering of the positive-lens columns, the even positive-lens columns therefore focus on the grating webs while the odd positive-lens columns focus on the slits in the analysis grating $G_2$.

Furthermore, an embodiment of the x-ray device is preferred in which the lens grating is assembled from prisms which preferably have a triangular or trapezoidal base area, in particular with a symmetric trapezoidal form, in which two non-parallel sides include a base angle, and moreover are preferably in a regular arrangement. The use of prisms as optical elements for manipulating x-ray radiation has already been known from the technical field of x-ray microscopy and, accordingly, manufacturing methods for manufacturing appropriate optical elements already exist. Some of these manufacturing methods, such as e.g. the so-called reactive ion etching or the so-called LIGA (lithography, electroplating and molding, from the German: Lithographie, Galvanik and Abformung) method are, in principle, suitable for manufacturing a lens grating proposed here, even if some adaptations are to be undertaken to this end. However, advantageously, an independent production method need not be developed.

Here, more preferably, each positive lens of the lens grating is assembled from a plurality of prisms, wherein the positive lenses of the lens grating advantageously in each case have an identical design. As in the case of every positive lens, electromagnetic radiation, in this case x-ray radiation, should be deflected to a different extent in this case depending on the impact position on the positive lens which, in the case of the positive lenses of the lens grating, is achieved either by a spatially dependent variation of the number of prisms or by a spatially dependent variation in the embodiment of the prisms through which the x-ray radiation passes. In the case of the column-like design of the lens grating, the design of a positive-lens column in the longitudinal direction of the positive-lens column is preferably unchanging here, while the design perpendicular thereto varies and the refraction of the x-ray radiation caused by the positive-lens column, and therefore the deflection of the x-ray radiation, only occurs perpendicular to the longitudinal direction of the positive-lens column.

Moreover, it is preferable for the lens grating to be assembled from prisms in such a way that the prisms of adjacent positive-lens columns touch one another at the column boundaries on the wide base of the trapezoids. Moreover, the lens grating is preferably configured in such a way that the trapezoids of adjacent rows are disposed half-offset with respect to one another such that, as a result of this, elongate and, in particular, meandering structures are formed by the trapezoids.

In order to enable as simple an adjustment of the lens grating as possible, i.e. in particular to enable an alignment of the lens grating relative to the optical axis of the x-ray device and therefore relative to the coherence grating, to the phase grating, to the x-ray detector and, to the extent that this is present, to the analysis grating, the prisms forming the lens grating are moreover preferably positioned on a base plate and, in particular, formed thereon. Therefore, only the base plate is aligned during the adjustment and not the prisms themselves. Manufacturing a corresponding lens grating is also simplified hereby.

Furthermore, it is advantageous if the prisms are embodied as slanted prisms and, accordingly, are inclined relative to the surface normal of the base plate. That is to say that at least one lateral face of the prisms is not aligned parallel to the surface normal of the base plate. Here, the arrangement of the prisms on the base plate preferably has such a periodicity in a Y-direction across the surface normal that the pattern formed by the prisms on the upper side and the pattern on the lower side of the lens grating are offset by exactly one period. As a result, each passage with the same X-position along an X-direction perpendicular to the Y-direction contains exactly the same amount of prism material along the Y-direction independently of the Y-position thereof, and so only the material variation in the X-position acts on a light wave due to the low refraction in the x-ray range. To the light, it then appears as if the material height e.g. increases from 0 to 100% of the grating height within the width of the prisms in the X-direction i.e., for example, as if the material height has a gradient of 50:1=89° for an X-width of 1 μm and a material height of 50 μm.

In an advantageous development, the inclination of the prisms with respect to the surface normal of the base plate is characterized by an angle of inclination, the preferred value of which lies between 2° and 30° and, in particular, between 5° and 15°. In simulations, this embodiment variant was found to be advantageous.

Moreover, in accordance with one embodiment variant, the lateral faces of the prisms do not have planar but parabolic configuration. In this case, the lens grating is therefore formed by parabolic prisms.

In accordance with one embodiment variant of the x-ray device, the lens grating is assembled from a number of so-called clessidra lenses ("hour glass" lenses). The basic geometric configuration of such lenses is known per se and used in the x-ray microscopy specialist field for focusing the x-ray beam. Appropriate manufacturing methods for producing such lenses, which are also referred to as compound refractive x-ray lenses, are currently researched and developed at, inter alia, the Karlsruhe Institute of Technology (Institute of Microstructure Technology). However, for the lens grating, it is not the case that an individual clessidra lens is used for manipulating the radiation field. Rather, the lens grating is preferably provided by a regular arrangement of a multiplicity of clessidra lenses, wherein, in particular, clessidra lenses are in each case strung together in two orthogonal directions. Therefore, the clessidra lenses of the lens grating are preferably, firstly, stacked above one another and, secondly, strung together laterally.

It is also preferred that the clessidra lenses stacked over one another in the x-direction are assembled from slanted prisms inclined in the y-direction and the x-ray radiation is focused and therefore deflected in the x-direction with the help of the clessidra lenses.

In an advantageous development, the lens grating is formed by two sub-gratings, wherein the two sub-gratings preferably have an identical design and are preferably displaced in relation to one another in the x-direction for forming the lens grating. Here, the sub-gratings are preferably formed by a regular arrangement of clessidra lenses, wherein the clessidra lenses in this case are also preferably respectively strung together in two orthogonal directions, i.e., firstly, strung together laterally and, moreover, stacked one above the other.

Gold or nickel are preferably used as base material for the lens grating—this also depends on the manufacturing method—wherein gold is advantageously used if x-ray radiation with a photon energy between 50 keV and 100 keV is to be manipulated by way of the lens grating, whereas nickel is preferably intended to be manipulated for manipulating x-ray radiation with a photon energy in the range from 15 keV to 50 keV. Furthermore, silicon is expedient for a range from 10 keV to 30 keV and resist or plastic is expedient for a range from 10 keV to 20 keV, particularly in the case of production by way of reactive ion etching.

An x-ray device 2, described below in an example manner and depicted schematically in FIG. 1, comprises an x-ray source 4, a coherence grating $G_0$, a phase grating $G_1$, a lens grating $G_L$, an analysis grating $G_2$ and an x-ray detector 6 made of a number of pixels.

Like in the case of most optical devices, it is possible to assign a system axis or optical axis 8 to the design, which axis is arranged in the z-direction in the case of the example embodiment.

In the example embodiment, the individual optical elements of the x-ray device 2 have planar embodiment, are disposed along this optical axis 8 and in each case aligned perpendicular thereto.

Here, the x-ray device 2 is provided for obtaining medical differential phase-contrast images and, in order to examine a patient by way of this imaging method, the latter is positioned between the coherence grating $G_0$ and the phase grating $G_1$, preferably directly in front of the phase grating $G_1$. In the x-ray device 2 presented here, the metrological acquisition or rather the establishment of the spatial distribution of the phase shift caused by the patient is brought about according to the principle known per se.

The coherence grating $G_0$ has a grating period p0 and a grating thickness or height $h_0$, and serves to ensure a sufficient spatial coherence of the x-ray radiation used for the interferometric measurement process. Here, the coherence grating $G_0$ is typically positioned at a distance of approximately 10 cm from the x-ray source 4 and approximately has the dimensions of a postage stamp. Here, position and distance are selected in such a way that the coherence grating $G_0$ at least covers the x-ray detector 6 in accordance with the intercept theorem. Alternatively, provision is made to use an x-ray radiation source which is punctiform to a good approximation instead of an extended x-ray radiation source 4 and a coherence grating $G_0$. That is to say that if the extended x-ray radiation source 4 is used, the x-ray radiation source 4 in combination with the downstream coherence grating $G_0$ acts as actual radiation source for the interferometric design. Here, the x-ray radiation source 4 generates x-ray radiation with a photon energy of up to approximately 100 keV, and a height $h_0$ of 1000 μm and a grating period $p_0$ of 26.83 μm was selected for the coherence grating G0 consisting of gold (Au, Z=79).

The phase grating $G_1$ is disposed offset from the coherence grating $G_0$ at a distance $d_{01}$ of 1000 mm in the z-direction. This serves for generating a strip-shaped interference pattern, like in the Talbot-Lau interferometer described at the outset, and, to this end, comprises a strip-shaped structure, wherein the structure strips extend in the y-direction. Here, the phase grating $G_1$ is embodied in such a way that, to a good approximation, there is no absorption in the phase grating $G_1$ but that the regular structure of the phase grating $G_1$ either lets beams pass through said phase grating without influence or lets said beams experience a phase shift by a quarter wavelength, i.e. by $\pi/2$, by the phase grating $G_1$, depending on the region in which said beams are incident on the phase grating $G_1$. A value of 42 μm was selected for the height $h_1$ of the phase grating $G_1$. In this example embodiment, the value of the grating period $p_1$ of the phase grating $G_1$ manufactured from silicon (Si, Z=14) is 1.42 μm.

The lens grating $G_L$ is positioned offset from the phase grating $G_1$ at a distance $d_{1L}$ of 55.91 mm. Said lens grating has a height $h_L$ of approximately 60 μm and a grating period $p_L$ of 1.5 μm and serves for manipulating the x-ray radiation field emanating from the phase grating $G_1$. Here, the grating period $P_L$ reproduces the periodicity of the interference pattern, formed by the phase grating $G_1$, at the position of the lens grating $G_L$, while the periodicity of the structure of the lens grating $G_L$ is given by $N \times p_L$, where, in the example embodiment in accordance with FIG. 1, N has a value of 5 such that in each case five periods of the interference pattern are alternately focused and imaged on webs and on slits of the analysis grating $G_2$. In the case present here, a phase shift of $\pi/2$, i.e. a quarter of the wavelength at a photon energy of 65 keV, is brought about with the aid of the phase grating $G_1$. Alternatively, provision is also made for phase shift by half a wavelength, wherein, in this case, the value 2.84 µm is selected for the grating period $p_1$.

The analysis grating $G_2$ is in turn situated offset in the z-direction, wherein the distance $d_{L2}$ between the lens grating $G_L$ manufactured from gold and the analysis grating $G_2$ likewise manufactured from gold is 43.92 µm. A value of 400 µm was selected for the height h2 and a value of 7.81 µm was selected for the grating period $p_2$. Finally, disposed downstream of the analysis grating $G_2$, which comprises a strip-shaped structure made of webs and slits, is the x-ray detector 6. Here, the grating heights are relatively uncritical. By contrast, the grating periods and the distances between the gratings must be exactly matched to one another because the design otherwise even increases the required radiation dose. Moreover, moiré effects between the lens grating $G_L$ and the analysis grating $G_2$ or the x-ray detector 6 are to be avoided, while corresponding effects between the phase grating G1 and the lens grating $G_L$ are less problematic. That is to say that, in particular, the distances $d_{01}$, $d_{1L}$, $d_{12}$ and the grating periods $p_L$ and $p_2$ must be predefined very exactly and must be matched to one another.

The extents of the gratings $G_1$, $G_L$, $G_2$ in the x-direction and in the y-direction are substantially equal; however, in an alternative embodiment, the extent of the lens grating $G_L$ in the x-direction and in the y-direction corresponds to the extent of the x-ray detector 6, i.e. to the detector area spanned by the pixels of the x-ray detector 6.

The functional principle of the design and, in particular, the effect of the lens grating in the x-ray device 2 can be understood on the basis of a simplified consideration on the basis of geometric optics. In this case, a punctiform x-ray radiation source at a slit of the coherence grating $G_0$ is considered, from which x-ray radiation is emitted in the direction of the phase grating $G_1$. The x-ray radiation depicted by beams then impinges on the phase grating $G_1$, wherein, alternately, a beam depicted by dashes experiences a phase shift and a beam characterized by a full line passes through the phase grating $G_1$ without being influenced. In more detail, near field interference occurs between the phase grating $G_1$ and the lens grating $G_L$ and a strip pattern is formed on the lens grating $G_L$ in accordance with the Talbot effect. By contrast, in accordance with the simplified point of view, straight-lined beams are assumed from the coherence grating $G_0$ through the phase grating $G_1$ to the lens grating $G_L$ in order to be able to describe the design more easily. By way of example, in the case of the maximum contrast, the beams uninfluenced by the phase grating $G_1$ (full lines) could transport the maximum intensity and the beams influenced in the phase by the phase grating $G_1$ (dashed lines) could transport minimum intensity.

Subsequently, the beams impinge on the lens grating $G_L$, where, as it were, there is a separation of the beams. In the process, five directly adjacent beams, which experienced a phase shift by the phase grating $G_1$, are in each case directed to an x-ray-radiation absorbing section, i.e. a web F2, of the analysis grating $G_2$ and, alternating therewith in the x-direction, five directly adjacent beams, which passed the phase grating $G_1$ without being influenced, are in each case deflected by the lens grating $G_L$ in such a way that they are incident on a non-absorbing section, i.e. a slit F1, of the analysis grating $G_2$. As an alternative to focusing five adjacent beams with the same phase onto a focus F, provision is made for focusing a different number N of adjacent beams with the same phase onto a focus F, wherein an odd number is preferred. As a result of this separating effect of the lens grating $G_L$, the analysis grating $G_2$ can be structured more coarsely than in the case of a Talbot-Lau interferometer according to the prior art, without this causing a significant change in the resolution capability or the visibility. Thus, while a value of approximately 1.5 to 2 µm is selected for the grating period $p_2$ in a Talbot-Lau interferometer according to the prior art having a comparable design but no lens grating $G_L$, the value of the grating period $p_2$ in the case of the example embodiment is approximately 8 µm.

Figure 2:
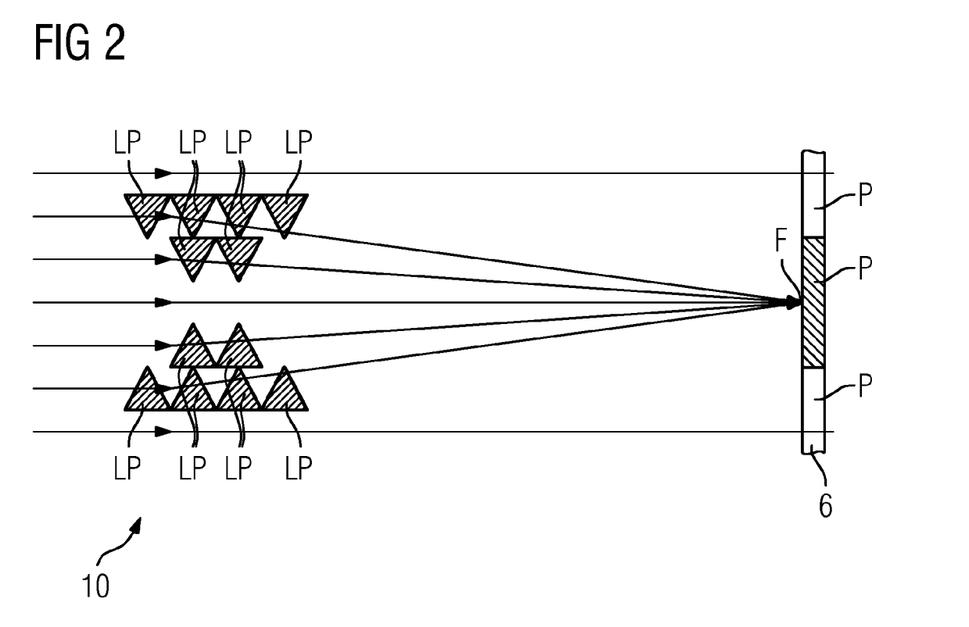
FIG. 2 shows a clessidra lens in a sectional illustration.

If the effect of the lens grating $G_L$ on five directly adjacent beams with the same phase is considered, then this corresponds to the effect of a positive lens, at the focus F of which the analysis grating $G_2$ is positioned. In order to focus x-ray radiation, it is known to make use of a so-called clessidra lens 10, as is depicted in FIG. 2. It is formed by a plurality of prisms, typically with a triangular base area, which are arranged in the form of an hour glass. The deflection of the x-ray radiation due to refraction at the prisms increases as the distance between the center of the hour glass form and the point at which x-ray radiation impinges on the clessidra lens 10 increases, as a result of which an effect corresponding to that of a positive lens is obtained.

Such a clessidra lens 10 forms a possible basis for designing the lens grating $G_L$, wherein the lens grating $G_L$ is assembled from two sub-gratings, of which one serves to deflect the beams which have experienced a phase shift by the phase grating $G_1$ while the other sub-grating serves to deflect those beams which passed the phase grating $G_1$ without being influenced.

Figure 1:
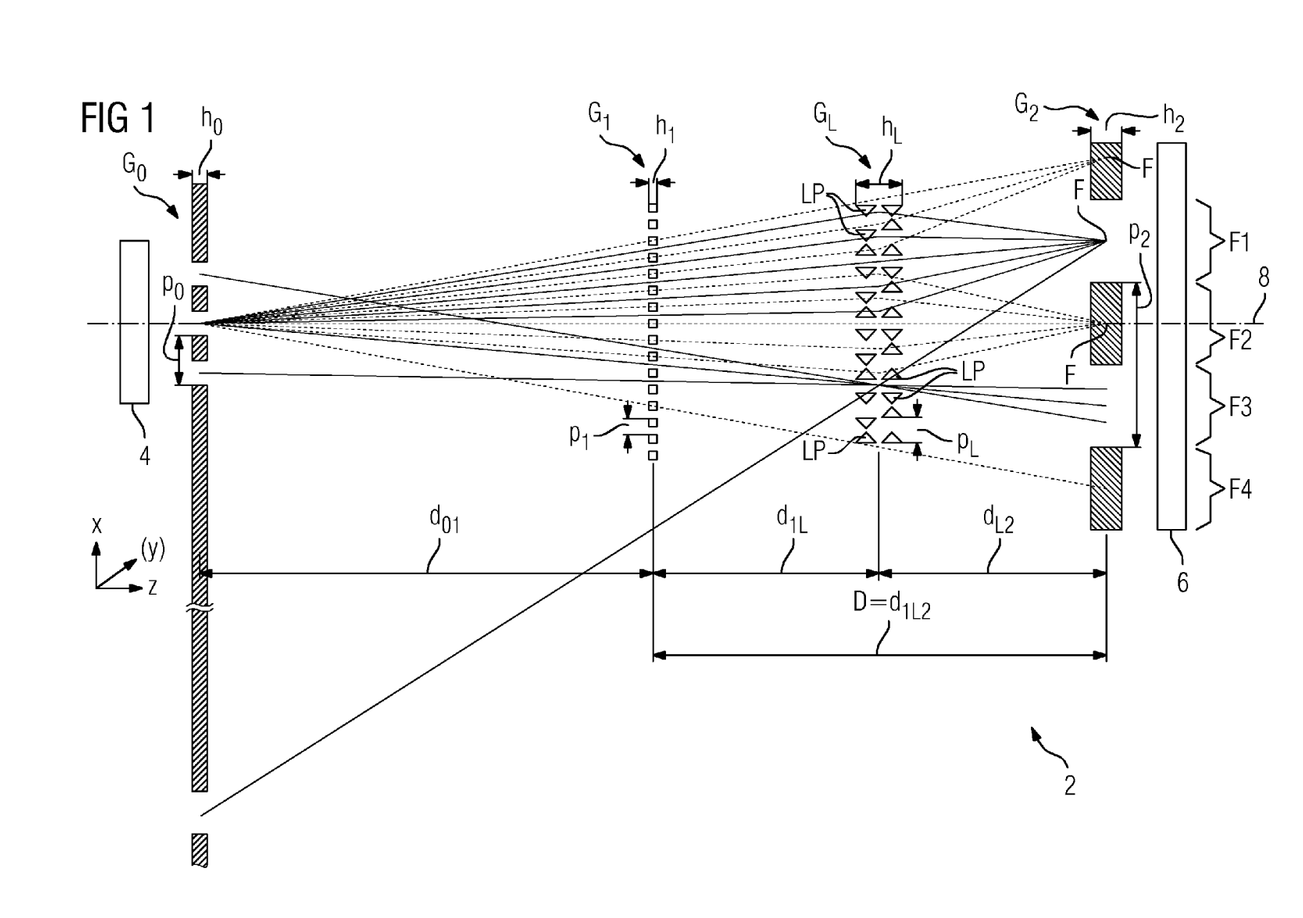
FIG. 1 shows an x-ray device with a lens grating in a sectional illustration.

In the example embodiment in accordance with FIG. 1, each positive lens, in an example manner, focuses five directly adjacent beams with the same phase. Here, these five beams symbolically represent five adjacent strips with the same intensity of the interference pattern level with the position of the lens grating $G_L$. The number N of strips with the same intensity in the interference pattern at the position of the lens grating $G_L$, which strips are imaged on a focus F by way of a positive lens of the lens grating $G_L$, is determined and prescribed by the design of the lens grating $G_L$ and, in particular, by the design of the positive lenses of the lens grating $G_L$.

If further slits of the coherence grating $G_0$ are also considered, what is found is that the beams thereof contribute to smearing of the image level with the analysis grating $G_2$. That is to say, the beams no longer coincide at one focus point F, but are incident on the respective web or the respective slit of the analysis grating $G_2$ with a slight offset with respect to one another in the x-direction, as indicated for the slit F3.

This effect becomes ever more pronounced, the more adjacent slits on the coherence grating $G_0$ are opened and accordingly emit x-ray radiation in the direction of the phase grating $G_1$. However, since the intensity of x-ray radiation available for an examination is also predetermined by this number, a suitable compromise needs to be selected in this case for the number of employed slits on the coherence grating $G_0$. However, further slits on the coherence grating $G_0$ can in turn be opened at a distance corresponding to a whole-line multiple of the grating period $p_0$ of the coherence grating $G_0$, without the imaging level with the analysis grating $G_2$ deteriorating, i.e. without the foci smearing. That is to say a second coherence condition is specified for the spatial coherence of the light source made of x-ray radiation source 4 and coherence grating $G_0$.

Figure 3:
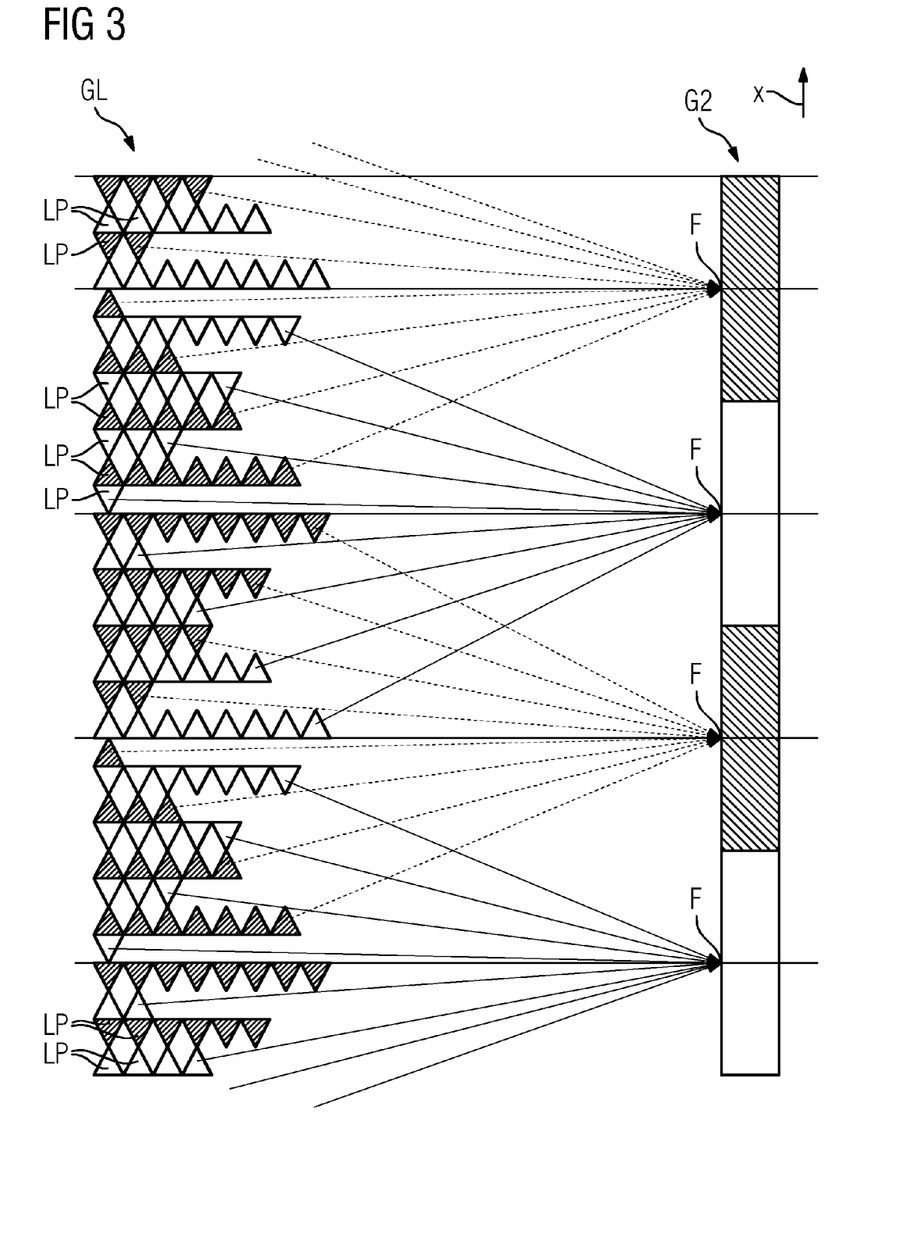
FIG. 3 shows an alternative embodiment of the lens grating in a sectional illustration.
Figure 4:
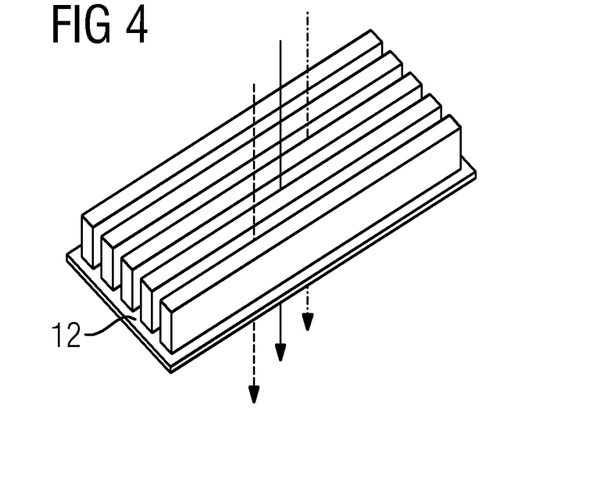
FIG. 4 shows an optical grating in a perspective view.

FIG. 3 shows, in an example manner, the effect of a lens grating $G_L$ assembled from individual prisms in a sectional illustration, wherein the prisms LP of one sub-grating are depicted in black and the prisms LP of the other sub-grating are depicted in a striped manner. Each sub-grating is formed by a multiplicity of clessidra lenses 10 which are arranged next to one another in the x-direction or stacked one above the other, and the two sub-gratings are displaced by half an extent of a clessidra lens 10. In the case of an odd factor N, such as e.g. N=5 in accordance with FIG. 1, they then fit perfectly into one another, whereas in the case of an even factor N, such as e.g. N=8 in accordance with FIG. 3, they need additionally to be displaced by half a grating period pL in order to fit into one another. Here, what the displacement of the sub-gratings with respect to one another brings about is that the respective sub-grating merely acts on beams which pass the phase grating G1 with the same phase and what this also brings about is that the beams with different phases are focused on different regions of the analysis grating $G_2$.

Thus the prisms LP, depicted in black, of the one sub-grating bring about a refraction of the beams phase shifted by the phase grating $G_1$, wherein in each case eight directly adjacent beams with the same phase are focused on a section of the analysis grating $G_2$ depicted in black which, for example, is embodied as a web and absorbs the incident x-ray radiation. By contrast, the other sub-grating formed by the striped prisms LP serves to refract the x-ray radiation which passed through the phase grating $G_1$ without being influenced, wherein in each case eight adjacent beams with the same phase are focused on the striped regions of the analysis grating $G_2$ which, for example, represent slits and through which the x-ray radiation can pass without hindrance. Here, in the two sub-gratings, two adjacent foci are spaced apart by half a grating period $p_2$ of the analysis grating $G_2$.

In accordance with an alternative embodiment variant, the use of the analysis grating $G_2$ is dispensed with and the x-ray detector 6 is positioned at the position of the analysis grating $G_2$, wherein the pixel size and/or the pixel spacing corresponds to half the grating period $p_2$. The design then substantially corresponds to the design in accordance with FIG. 3, wherein the striped structure elements and the structure elements depicted in black of the analysis grating $G_2$ are in each case replaced by pixels P of the x-ray detector 6. The embodiment variant without analysis grating $G_2$ is provided, in particular, for mammography, wherein, in this case, use is made of x-ray radiation with a photon energy between 15 and 25 keV. Moreover, the lens grating $G_L$ is not manufactured from gold but rather from nickel in this case. Moreover, use is made of an x-ray detector 6, the pixels of which have an extent of between 20 μm×20 μm and 50 μm×50 μm.

The lens gratings $G_L$ in accordance with FIG. 1 and FIG. 3 are assembled from identical prisms LP which have a triangular base area and are positioned with a regular arrangement relative to one another and relative to the optical axis 8 of the x-ray device 2. The prisms LP are formed onto a base plate 12 for the benefit of simpler manufacturing and simpler adjustment, i.e. alignment with respect to the optical axis 8. This assembly made of base plate 12 and formed-on lens prisms Lp is produced by way of e.g. the LIGA method specified at the outset and then aligned with respect to the optical axis 8. By contrast, the prisms LP themselves are aligned relative to one another by way of the forming onto the base plate 12.

Figure 5:
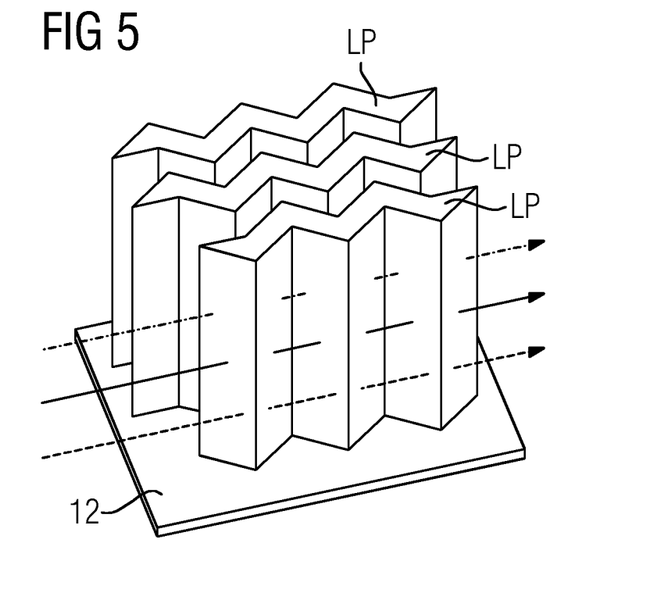
FIG. 5 shows a regular arrangement of prisms with an indicated alignment relative to an optical axis in a perspective view.
Figure 6:
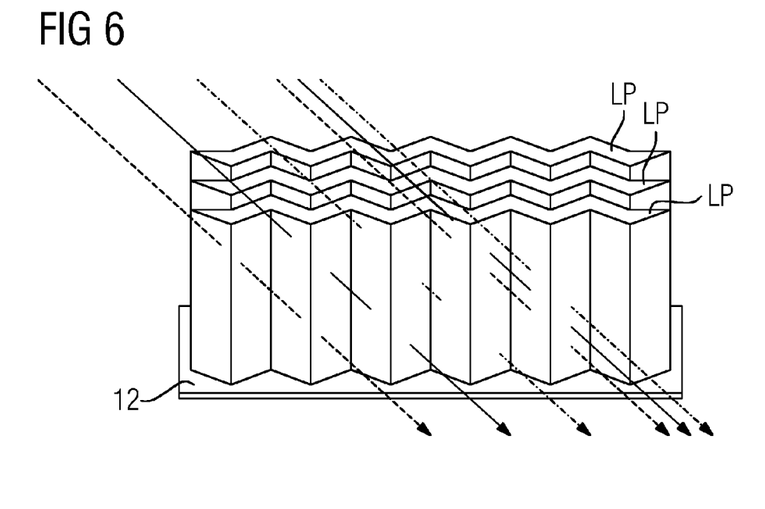
FIG. 6 shows the regular arrangement of prisms with an alternative alignment relative to the optical axis in a perspective view.
Figure 7:
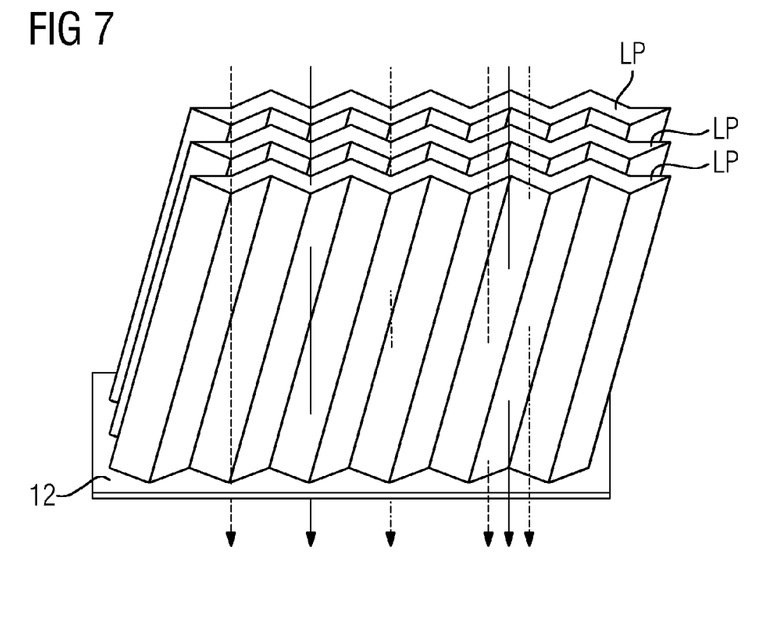
FIG. 7 shows an alternative regular arrangement of prisms with an alternative alignment relative to the optical axis in a perspective view.

FIG. 5 to FIG. 7 depict, in an example manner, three regular arrangements of prisms P and the arrows indicate the orientation of the base plate 12 relative to the optical axis 8 and therefore, to a good approximation, relative to the direction of the beams of the x-ray radiation. Here, FIG. 5 shows a disadvantageous arrangement with a field of view that is too small, while FIG. 6 and FIG. 7 show expedient arrangements, as are envisaged for the design. Here, the prisms are only illustrative and do not yet reproduce the specific embodiment of the lens grating. They merely show the arrangement in relation to the orientation with respect to the optical axis. Here, FIG. 6 shows a perpendicular prism structure, which is then positioned obliquely with respect to the optical axis in the design, while FIG. 7 shows a slanted, slantly manufactured prism structure such that the lens grating in this case is disposed perpendicular to the optical axis in the design.

As mentioned above, the lens grating $G_L$ is produced by way of e.g. the LIGA method and FIG. 11 to FIG. 15 depict various embodiments of masks, with the aid of which a lens grating $G_L$ presented here can be produced.

In the method, a gold mask is directly positioned over the resist, which for example has a thickness of 100 μm, and exposed to x-ray radiation. As a result of this filling regions, which are given by holes or trenches, detach from the resist for subsequent filling. In a subsequent electroplating process step, these filling regions are filled with a metal. The resist applied at the start of the LIGA process is depicted in white here and the electroplated metal is depicted in black.

Figure 8:
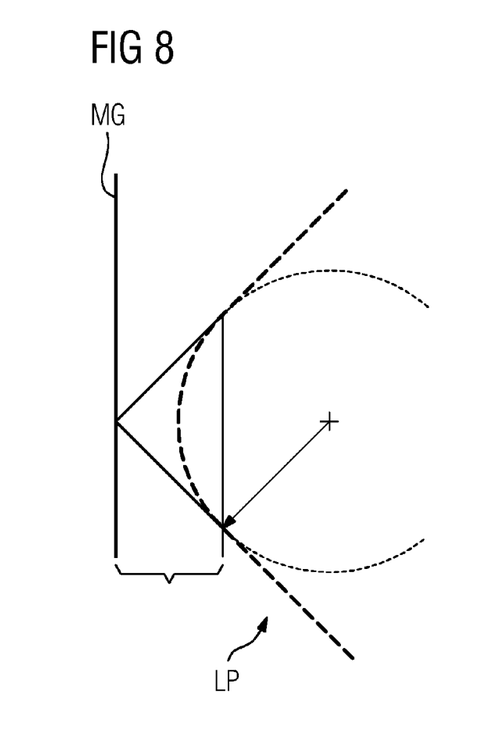
FIG. 8 shows a first embodiment of a prism base area in a sectional illustration.
Figure 9:
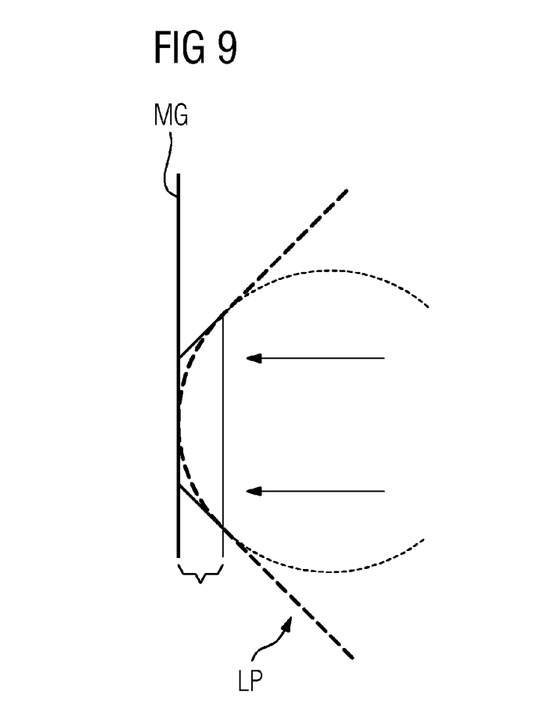
FIG. 9 shows a second embodiment of the prism base area in a sectional illustration.
Figure 10:
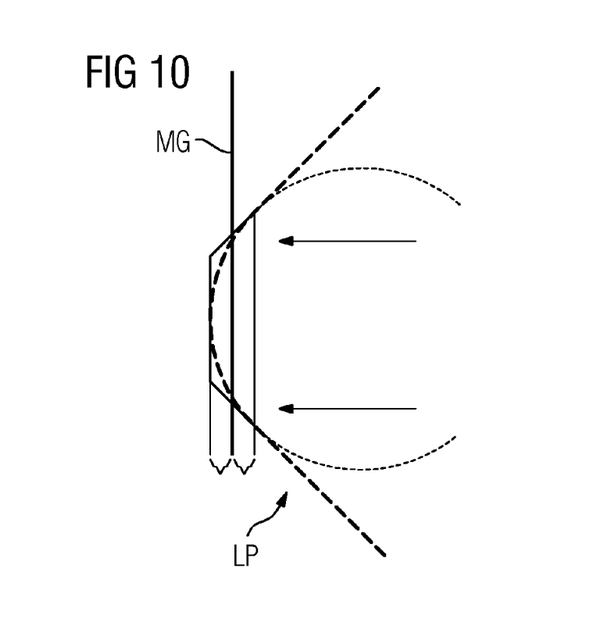
FIG. 10 shows a third embodiment of the prism base area in a sectional illustration.

The prisms LP of the regular arrangements in accordance with FIG. 5 to FIG. 7 have a triangular base area. However, depending on the production process, sharp edges can only be realized to a limited extent; instead, the corners have more of a round embodiment due to the production process and can therefore be represented by a circular segment. FIG. 8 shows the resulting round profile, i.e. which is present after manufacturing, at a slit boundary or material boundary MG for the case that a base area corner, depicted by the fine, full line, was planned up to the edge of the prism LP in a layout for a lithography mask. In the case of the shown 45° corner in the layout, it is nevertheless possible to come much closer to this prism boundary than is suggested by the radius. If the corner has a flatter design, it is approximated to an increasingly better extent by the circular segment. FIG. 9 shows a variant in which the material boundary MG can be brought up to the prism boundary by additional height in the y-direction. The variant shown in FIG. 10 is configured in such a way that the edge rounding comes to rest on the prism boundary. This allows adjacent round regions to be arranged above one another and therefore relate to a smaller region on the horizontal axis, wherein the grating structure was assumed to be on the vertical axis.

By way of the lithography masks depicted in FIG. 11 to FIG. 15, it is possible to realize lens gratings GL with a design made of positive lens columns. Here, the columns are aligned in the y-direction and the refraction of the x-ray radiation, i.e. the deflection of the beams, occurs in the x-direction. Depending on the x-position, the base areas of the prisms LP have different thicknesses or base angles and the prisms LP of in each case two or three adjacent strips or rows engage in one another in such a way that meandering structures, which are elongate in the y-direction, are formed, the rectangular markings denoted by the references A to D showing the prisms LP with different gradients, i.e. the prisms LP with different base angles. Moreover, oblique exposure is provided for the production, and so the prisms LP of the lens grating $G_L$ manufactured by way of this method are embodied as slanted prisms LP with an incline in the y-direction.

Here, the arrangement of the prisms LP on the base plate has such a periodicity in the y-direction that the pattern formed by the prisms LP on the upper side and the pattern on the lower side of the lens grating $G_L$ are offset by exactly one period $p_y$. As a result, each passage with the same x-position along the x-direction perpendicular to the y-direction contains exactly the same amount of prism material along the y-direction independently of the y-position thereof, and so only the material variation in the x-position acts on a light wave due to the low refraction in the x-ray range.

In the process, the x-ray radiation as it were sees perpendicular to the x-direction and perpendicular to the y-direction through the lens grating $G_L$ when passing through in the z-direction, which can be identified when observing the lithography mask in the y-direction, namely that the change of the effective path length through the prism material is more pronounced when varying the x-position in the case of steeper prisms A than in the case of less steep prisms D or in the case of flat prisms B. Here, the prisms LP within a positive lens column become increasingly steeper with increasing distance in the x-direction from a column center SM and, accordingly, the x-ray radiation is refracted or deflected more strongly in the direction of the column center SM. At the lower edge of the lithography masks in FIG. 11 to FIG. 13, full and dashed arrows indicate the x-positions at which the beams in accordance with the simplified explanation of the functional principle in accordance with FIG. 1 with N=5 impinge on the lens grating $G_L$.

Figure 11:
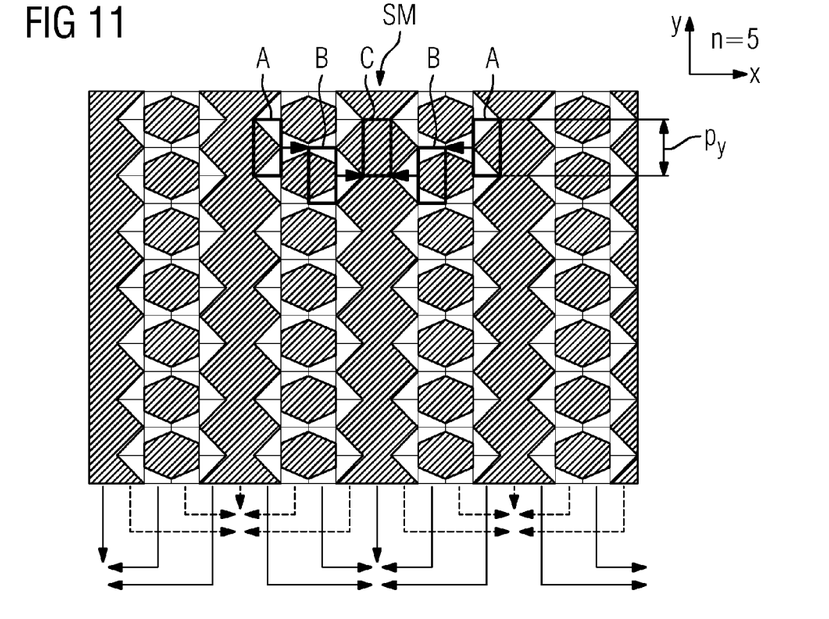
FIG. 11 shows a first layout of a lithography mask in a top view.
Figure 12:
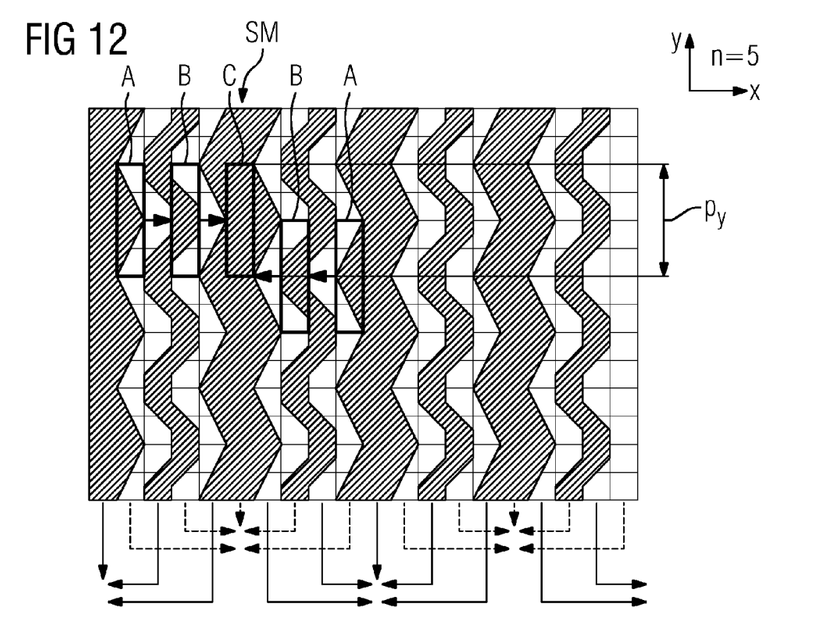
FIG. 12 shows a second layout of the lithography mask in a top view.
Figure 13:
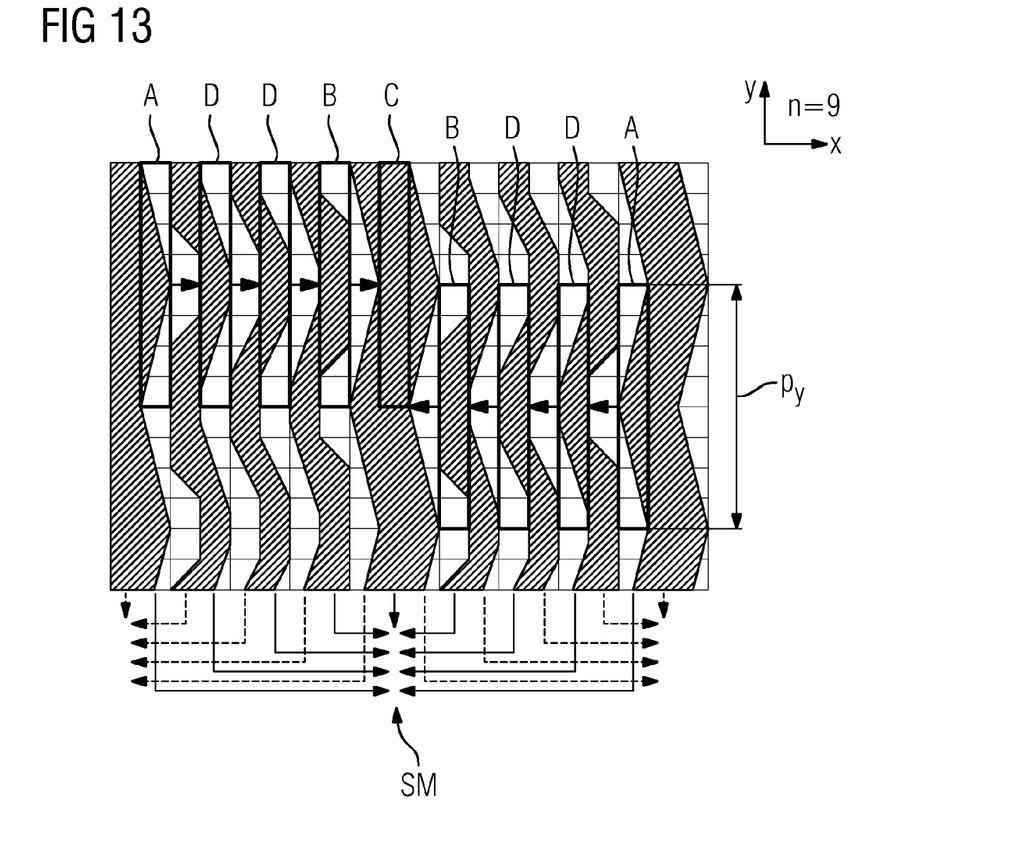
FIG. 13 shows a third layout of the lithography mask in a top view.
Figure 14:
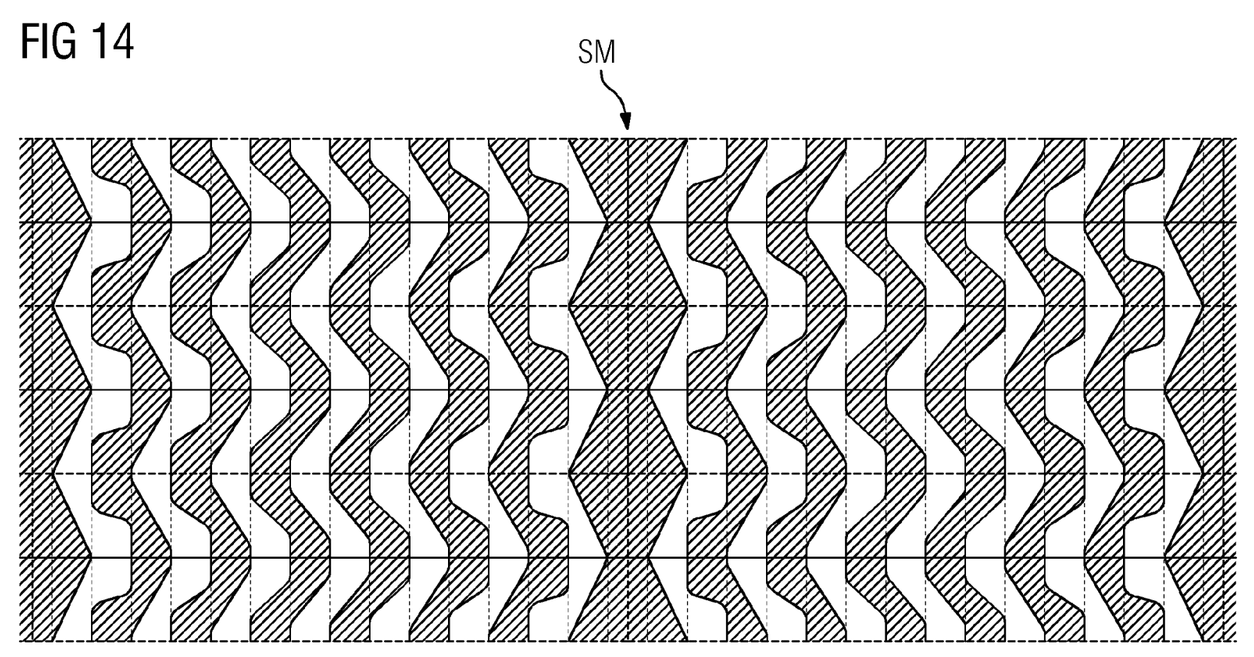
FIG. 14 shows a fourth layout of the lithography mask in a top view and FIG. 15 shows the fourth layout of the lithography mask in a magnified view.
Figure 15:
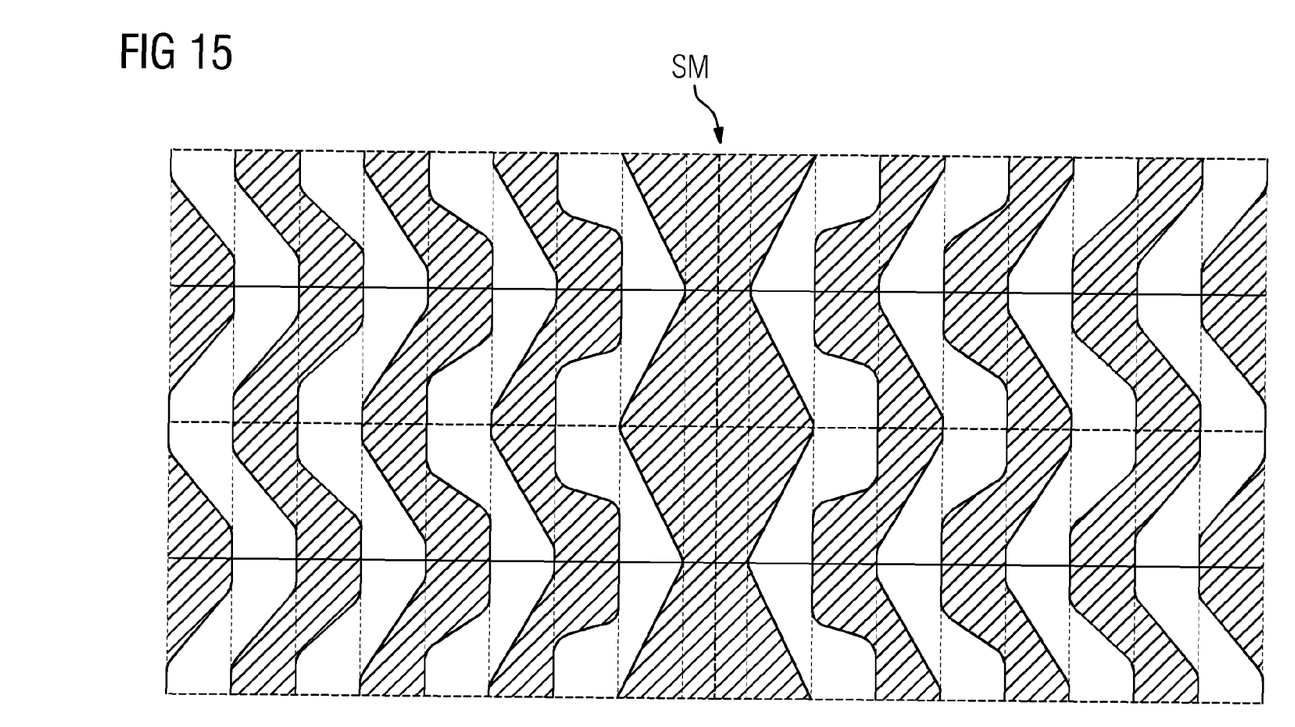

Here, in FIG. 11 and FIG. 12, in each case five directly adjacent beams of one phase are indicated by full arrows, while the five adjacent beams of the other phases are symbolized by dotted arrows. By contrast, in FIG. 13, in each case nine beams with the same phase are focused in the x-direction through a positive lens column onto a focus level with the column center SM.

The invention is not restricted to the example embodiment described above. Rather, a person skilled in the art is also able to derive other variants of the invention herefrom without departing from the scope of the invention. In particular, it is moreover also possible to combine all individual features described in conjunction with the example embodiment in different ways without departing from the subject matter of the invention.

The invention claimed is:

1. An x-ray device, comprising:
   an x-ray radiation source;
   a coherence grating;
   a phase grating; and
   an x-ray detector made of a number of pixels disposed in a matrix-like manner; and
   a lens grating assembled from prisms, wherein the lens grating is disposed between the phase grating and the x-ray detector and the lens grating includes two sub-gratings arranged in an optical axis direction, of which a first sub-grating deflects x-ray beams which have experienced a phase shift by the phase grating and a second sub-grating deflects x-rays beams which passed the phase grating without being influenced.

2. The x-ray device of claim 1, wherein a focus plane is assigned to the lens grating and wherein the x-ray detector is positioned in the focus plane.

3. The x-ray device of claim 1, further comprising:
   an absorption grating, positioned between the lens grating and the x-ray detector.

4. The x-ray device of claim 3, wherein a focus plane is assigned to the lens grating and wherein the absorption grating is positioned in the focus plane.

5. The x-ray device of claim 1, wherein the prisms include a triangular or trapezoidal base area.

6. The x-ray device of claim 1, wherein the prisms include a regular arrangement.

7. The x-ray device of claim 6, wherein the regular arrangement of prisms comprises prisms with different base areas.

8. The x-ray device of claim 6, wherein, in each case, a plurality of prisms mesh in such a way that elongate meandering structures are formed in an optical axis direction.

9. The x-ray device of claim 1, wherein the prisms are formed onto a base plate.

10. The x-ray device of claim 9, wherein at least one lateral face of the prisms is inclined with an angle of inclination of between 5° and 15° with respect to the surface normal of the base plate.

11. The x-ray device of claim 1, wherein the prisms are embodied as slanted prisms.

12. The x-ray device of claim 1, wherein the lens grating is assembled from a number of clessidra lenses.

13. The x-ray device of claim 1, wherein gold, nickel or silicon is used as the main material for the lens grating.

14. The x-ray device of claim 1, wherein the x-ray device is for phase-contrast imaging in the medical sector.

15. The x-ray device of claim 1, wherein the lens grating includes an arrangement of positive lenses, each lens configured to focus x-ray radiation to precisely one pixel of the x-ray detector.

16. The x-ray device of claim 1, wherein the lens grating comprises a regular arrangement of columns of positive lenses focusing in one dimension, wherein each one of the columns of positive lenses focuses x-ray radiation in the scope thereof onto precisely one column of pixels of the x-ray detector.

* * * * *